United States Patent
Korpimaki et al.

(10) Patent No.: US 7,972,838 B2
(45) Date of Patent: Jul. 5, 2011

(54) METHOD FOR STABILIZING ASSAY REAGENTS, REAGENT CONTAINER WITH STABILIZED ASSAY REAGENTS AND USE THEREOF

(75) Inventors: Teemu Korpimaki, Turku (FI); Timo Lovgren, Turku (FI); Jussi Nurmi, Parainen (FI)

(73) Assignee: Abacus Diagnostica Oy, Turku (FI)

( * ) Notice: Subject to any disclaimer, the term of this patent is extended or adjusted under 35 U.S.C. 154(b) by 1108 days.

(21) Appl. No.: 11/628,354

(22) PCT Filed: Jun. 3, 2005

(86) PCT No.: PCT/FI2005/050194
§ 371 (c)(1),
(2), (4) Date: Feb. 22, 2007

(87) PCT Pub. No.: WO2005/118849
PCT Pub. Date: Dec. 15, 2005

(65) Prior Publication Data
US 2007/0243601 A1    Oct. 18, 2007

Related U.S. Application Data

(60) Provisional application No. 60/576,820, filed on Jun. 4, 2004.

(30) Foreign Application Priority Data

Jun. 4, 2004    (FI) ..................................... 20040768

(51) Int. Cl.
C12M 1/34    (2006.01)
C12M 1/00    (2006.01)
(52) U.S. Cl. .................................................. 435/287.9
(58) Field of Classification Search .... 435/287.1–287.9; 427/2.13
See application file for complete search history.

(56) References Cited

U.S. PATENT DOCUMENTS
4,162,003 A    7/1979    Bartos et al. .................. 206/219
(Continued)

FOREIGN PATENT DOCUMENTS
EP    0 674 009    9/1995
(Continued)

OTHER PUBLICATIONS

Nurmi et al., "High-Throughput Genetic Analysis Using Time-Resolved Fluorometry and Closed-Tube Detection," 229 *Anal. Biochem.* 211-217 (2001).

(Continued)

*Primary Examiner* — Walter D Griffin
*Assistant Examiner* — Shanta G Doe
(74) *Attorney, Agent, or Firm* — James C. Lydon

(57) ABSTRACT

A reagent container having an inner surface upon which at least two reagents are dried, with the first reagent dried on a first area separate from a second area where the second reagent is dried. The first and second reagents are a nucleic acid polymerase and its substrate. A method is disclosed which includes dispensing at least the first and second reagents onto separate areas of the inner surface of the reagent container, and removing excess water from the reagents. The reagent container can be used in a polymerase chain reaction (PCR) assay, an assay that utilizes a reverse transcriptase, a reverse transcriptase polymerase chain reaction, an immuno-PCR assay, a nucleic acid sequence based assay, a proximity ligation assay, a ligase chain reaction assay, a rolling circle amplification assay, and a strand displacement amplification assay.

13 Claims, 3 Drawing Sheets

U.S. PATENT DOCUMENTS

| | | | |
|---|---|---|---|
| 4,351,158 A | 9/1982 | Hurwitz et al. | 62/60 |
| 5,229,297 A | 7/1993 | Schnipelsky et al. | 436/94 |
| 5,834,254 A | 11/1998 | Shen et al. | 435/91.2 |
| 5,948,673 A * | 9/1999 | Cottingham | 435/287.2 |
| 6,187,598 B1 * | 2/2001 | May et al. | 436/514 |
| 6,300,068 B1 * | 10/2001 | Burg et al. | 435/6 |
| 7,238,538 B2 * | 7/2007 | Freitag et al. | 436/514 |
| 2002/0058329 A1 * | 5/2002 | Singh et al. | 435/287.2 |

FOREIGN PATENT DOCUMENTS

| | | |
|---|---|---|
| EP | 0 726 310 | 8/1996 |
| EP | 0 834 729 | 4/1998 |
| FR | 2674253 | 9/1992 |
| WO | WO 01/92569 | 12/2001 |

OTHER PUBLICATIONS

Lovgren et al., "One-step All-in-one Dry Reagent Immunoassays With Fluorescent Eropium Chelate Label and Time-Resolved Fluorometry," 42 *Clin. Chem.* 1196-1201 (1996).

* cited by examiner

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
gcggagcaag cttcgtacct tct                                         23

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
ctaacgccca gaacaccgat tgagt                                       25

```
<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
ccataccagg acggcagttc tcagc                                          25

<210> SEQ ID NO 4
<211> LENGTH: 17
<212> TYPE: DNA
<213> ORGANISM: Artificial Sequence
<220> FEATURE:
<223> OTHER INFORMATION: Quencher probe

<400> SEQUENCE: 4
ctgccgtcct ggtatgg                                                   17

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
tgaaccagag gagttcttgc a                                              21

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
cccagaatca cccgagcga                                                 19

<210> SEQ ID NO 7
<211> LENGTH: 25
<212> TYPE: DNA
<213> ORGANISM: Artificial Sequence
<220> FEATURE:
<223> OTHER INFORMATION: Probe
<220> FEATURE:
<221> NAME/KEY: modified_base
<222> LOCATION: (1)..(1)
<223> OTHER INFORMATION: amino modified

<400> SEQUENCE: 7
cccttctgag ggtgattgcg cactg                                          25

<210> SEQ ID NO 8
<211> LENGTH: 18
<212> TYPE: DNA
<213> ORGANISM: Artificial Sequence
<220> FEATURE:
<223> OTHER INFORMATION: Quencher probe
<220> FEATURE:
<221> NAME/KEY: modified_base
<222> LOCATION: (17)..(17)
<223> OTHER INFORMATION: amino modified
```

-continued

<400> SEQUENCE: 8
aatcaccctc agaaggct                                                18

METHOD FOR STABILIZING ASSAY REAGENTS, REAGENT CONTAINER WITH STABILIZED ASSAY REAGENTS AND USE THEREOF

This application is the U.S. National Stage of International Application No. PCT/FI2005/050194, filed Jun. 3, 2005, which claims benefit of U.S. Provisional Application No. 60/576,820, filed Jun. 4, 2004, and Finnish Application No. 20040768, filed Jun. 4, 2004.

FIELD OF THE INVENTION

The present invention relates to a method for stabilizing biological and chemical detection reagents in a dry form.

BACKGROUND OF THE INVENTION

The publications and other materials used herein to illuminate the background of the invention, and in particular, cases to provide additional details respecting the practice, are incorporated by reference.

In vitro analytical methods that allow the detection of specific analyte molecules—small molecules, electrolytes, proteins, lipids, carbohydrates or nucleic acids—or even microorganisms such as bacteria, viruses, fungi or protozoan organisms—are essential for modern human and veterinary medicine, control of the environment, monitoring of food safety and all other fields of biological research. In many analytical techniques, detection is at least partly based on nucleic acid amplification. Examples of nucleic acid amplification techniques include but are not limited to the polymerase chain reaction (PCR) (Saiki et al., 1985), nucleic acid sequence based amplification (NASBA) (Compton, 1991), reverse transcription PCR, and real-time PCR (Higuchi et al., 1992 and 1993). While nucleic acid amplification techniques are used to detect nucleic acid analytes, techniques exist that combine a nucleic acid assay and a different ligand binding assay. In such combination methods, nucleic acid amplification is used in the detection of a molecule such as a protein or other non-nucleic acid molecule. Examples of combination methods that comprise a nucleic acid amplification step include the immuno-polymerase chain reaction (Niemeyer et al., 2005) and the proximity ligation assay (Fredriksson et al., 2002).

Analytical assays in general can be heterogeneous, which means that at least one of the assay components is bound to a solid support and at least one of the assay components is in solution, or homogeneous, which means that all assay components are in solution. Such analytical techniques often require several pipetting steps to combine a set of detection reagents with the samples. These pipetting steps, if performed manually, constitute an important source of analytical error, especially in the case of assays in which small variations in assay component concentrations cause significant error (such as competitive immunoassays), and require a considerable amount of hands-on time. If the pipetting steps are automated, as is often done, the errors due to human actions as well as the amount of manual work can be minimized but, on the other hand, expensive equipment is needed for liquid handling. To make analytical techniques, that have a step where a sample is combined with a set of detection reagents, simpler, faster, more reliable and applicable even outside a specialized laboratory environment, it is possible to pre-dispense the detection reagents into a container, after which excess water is removed and the reagents are stored in a dry form. The dry reagent container will subsequently act as a reaction vessel also. Thus, carrying out the assay requires a minimum of liquid handling steps: only a sample in a suitable volume of a suitable liquid needs to be added into a vessel that already contains the dried detection reagents. Upon sample addition, the dried reagents are again dissolved and the analysis can begin. Such all-in-one dried assay reagents have been applied to for example immunoassays (Lövgren et al., 1996) and PCR assays (Nurmi et al., 2001).

Many biological and chemical reagents are stable in a dry form. However, a problem that is sometimes encountered is that the composition of detection reagents, when dried as a mixture, is unstable even if all components, when dried individually, would be stable. This instability may, for example, be caused by one or more of the reagents acting upon one or more of the other reagents during drying or storage in a manner that adversely affects the stability of the reagents One way to overcome this problem is to place an insulating layer between different reagents and thereby prevent any adverse reactions between different assay components. This kind of an approach has been described in the prior art (WO9738311, Lövgren et al. 1996). By separating at least one of the reagents that take part in the unwanted reactions, the reagent mixture can be stabilized. However, this approach requires the addition of an insulating layer, which introduces some problems to the manufacturing process. First of all, the reagent added after the insulating layer has to be dispensed in as small a volume as possible in order to avoid dissolving the insulating layer. Small volume dispensing is quite prone to variation, so assay analytical error can increase as a result. Furthermore, in some applications, it may be impossible to find a suitable composition for an insulating layer, since some of the components of the insulating layer itself may adversely affect the detection assay. Thus the production of dry reagents would be simpler, less prone to error and more often possible, if no insulating layer was needed. Another problem encountered when drying assay reagents is the method of drying itself: usually, lyophilization is used. Lyophilization, however, is a technically more demanding process than air-drying and it would be advantageous to have a way of stabilizing assay reagents so that air-drying could be used to remove excess water from the reaction mixtures instead of lyophilization.

In some assays that comprise a nucleic acid amplification step utilizing a nucleic acid polymerase, it is possible to dry the reagents as a mixture without any unwanted side reactions. An example of a fully functional assay in which all reagents are dried as a mixture has been published by for example Nurmi et al. (2001). However, in other cases, some nucleic acid polymerases exhibit unwanted side reactions or are otherwise unstable when they are dried together with other assay reagents. To solve this problem, a method is needed that allows stabilization of such reagent mixtures.

OBJECT AND SUMMARY OF THE INVENTION

One object of the present invention is to provide a reagent container with stabilized reagents for assays employing nucleic acid polymerase as a reagent.

Another object of the present invention is to provide a method for stabilizing chemical or biological reagents for the detection and/or quantitation of biological or chemical analytes for assays employing nucleic acid polymerase as a reagent.

Yet another object of the present invention is to provide uses of a reagent container with stabilized reagents in assays employing nucleic acid polymerase as a reagent.

The present invention provides a reagent container for detection and/or quantitation of at least one biological or chemical analyte from a sample, said reagent container comprising an inner surface enclosing a volume, wherein volume analytical reactions of at least one analysis for detection and/or quantitation of at least one analyte take place, and at least two reagents of an analysis of an analyte have been dried onto said inner surface and at least a first said reagent has been dried onto a first area of the inner surface distinctly separate, i.e. without any overlap, from a second area of the inner surface onto which at least a second said reagent has been dried. Characteristic for the reagent container is that the first reagent and the second reagent form a pair wherein the first reagent is an enzyme and the second reagent is a substrate of said enzyme, and said pair consists of a nucleic acid polymerase and substrate thereof.

The present invention also provides a method for stabilising onto an inner surface of a reagent container dried assay reagents for the detection and/or quantitation of a biological or chemical analyte from a sample, said method comprising the steps of
a) dispensing at least two reagents, a first reagent and a second reagent, needed in the detection of the analyte onto the inner surface of the reagent container, and
b) removing excess water from the reagents,
wherein in step a) the first reagent is dispensed onto a first area of the inner surface distinctly separate, i.e. without any overlap, from a second area of the inner surface onto which the second reagent is dispensed. Characteristic for the method is that the first reagent and the second reagent form a pair wherein the first reagent is an enzyme and the second reagent is a substrate of said enzyme, and said pair consist of a nucleic acid polymerase and substrate thereof.

The present invention further provides the use of the reagent container according to the invention to perform an assay selected from the group consisting of a polymerase chain reaction (PCR) assay, an assay that utilizes a reverse transcriptase, a reverse transriptase polymerase chain reaction, an immuno-PCR assay, a nucleic acid sequence based assay (NASBA), a proximity ligation assay, a ligase chain reaction (LCR) assay, a rolling circle amplification (RCA) assay, and a strand displacement amplification (SDA) assay.

BRIEF DESCRIPTION OT THE DRAWINGS

DETAILED DESCRIPTION OF THE INVENTION

Figure 1:
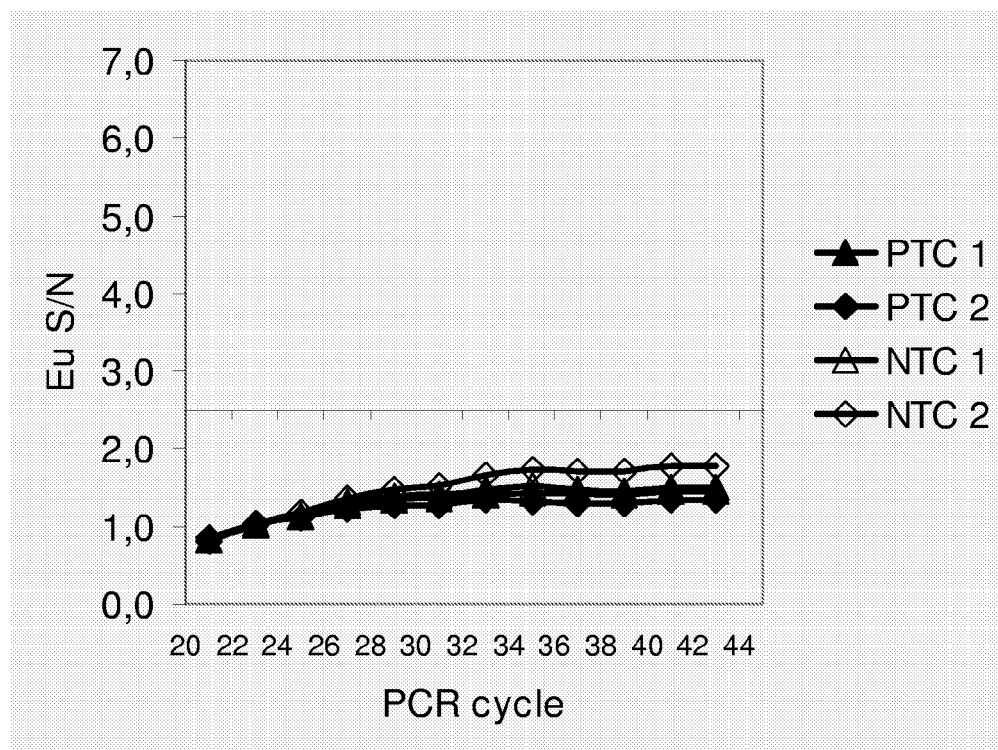
FIG. 1 shows instability of PCR reagents dried as a mixture.

The term reagent container as used herein refers to a container in which reagents are stored. In the context of the present invention, the reagent container comprises a volume that can function as a reaction chamber. Typically reagents are dispensed to, dried and stored in the reagent container that, subsequently, can act as a vessel where an analytical reaction takes place.

The term analyte as used herein refers to any substance or living organism or part of a dead or living organism or a virus or a part of a virus, the presence or amount of which is to be measured in a sample of any kind.

The term sample used herein refers to any part taken of what is to be analysed. It can also refer to such a part already diluted in a known proportion to a diluent, typically a buffer or solvent, such as water.

The term reagent as used herein refers to any individual substance or composition of different substances that is required to determine the presence and/or amount of an analyte in a sample.

The term enzyme as used herein refers to any chemical moiety capable of catalysing a chemical reaction. An enzyme is typically a protein, formed in a living organism or synthetic, that acts as a catalyst.

The term substrate of an enzyme as used herein refers to a substance that can, in suitable conditions, be a reactant of a chemical reaction catalysed by the enzyme. In an assay, a substrate can be an analyte and/or a reagent.

The term nucleic acid polymerase as used herein refers to any chemical moiety capable of catalysing the synthesis or breakdown of nucleic acids or nucleic acid derivatives. Examples of such nucleic acid polymerases include but are not limited to DNA polymerase, reverse transcriptase, RNA polymerase, DNA ligase and RNA ligase.

The term binding agent as used herein refers to any molecule capable of forming at least one covalent or non-covalent bond with a second molecule. Examples of binding agents include but are not limited to immunoglobulins and derivatives thereof, such as recombinant antibodies, Fab fragments and scFv fragments; nucleic acid binders such as nucleic acids and nucleic acid derivatives and aptamers and DNAzymes and ribozymes; and proteins capable of binding specific ligands.

The term ligand as used herein refers to any molecule capable of forming at least one covalent or non-covalent bond with a binding agent. A ligand can be naturally occurring or synthetic. In an assay, a ligand can be the analyte and/or a reagent needed in the detection of the analyte.

The term reverse transcriptase, as used herein, refers to any chemical moiety capable of catalysing the synthesis of deoxyribonucleic acid using ribonucleic acid or deoxyribonucleic acid as a template.

The phrase removing excess water, as used herein, refers to any method of reducing the amount of water inside a reagent container. As will be appreciated by those skilled in the art, a number of ways exist for reducing the amount of water. Preferably, excess water is removed by air-drying. Examples of other suitable methods include but are not limited to vacuum drying, heat drying and lyophilization.

The present invention relates to a method for stabilizing biological and chemical detection reagents in a dry form by dispensing the reagents into at least two spatially separated spots inside the same reaction container space before drying the reagents, thus physically separating one or more of the reagents from the rest of the reagents without using an insulating layer between the spots.

It is to be noted that a reagent container according to the invention can comprise more than two distinctly separate areas, whereon reagents have been dried. Thus, the reagent container can e.g. comprise a third, fourth or even twenty-first distinctly separate area whereon reagents have been dried. Such embodiments containing more than one area onto which reagents have been dried are preferable if more than two reagents have to be kept separate from each other in order to make sure that the reagents are stable during drying and/or storage.

According to a typical embodiment of the present invention, the assay reagents include at least one enzyme, i.e. a nucleic acid polymerase. Examples of suitable enzymes that can be included are but are not limited to oxidoreductases, transferases, hydrolases, lyases, ligases. For example, the composition of assay reagents may be suitable for performing a qualitative or quantitative assay for an analyte that is a) a reactant in,
b) an inhibitor of,
c) an activator of, or
d) protein, or
e) an enzyme capable of catalyzing a chemical reaction that takes place upon combining a sample containing said analyte with the composition of assay reagents. To stabilize the composition of such assay reagents in a dry form, an enzyme can be separated from at least one of the other assay reagents, at least one of the other assay reagents being, in a preferable embodiment, a substrate of the enzyme.

According to another typical embodiment of the present invention, the assay reagents include at least one substrate for an enzyme, i.e. a nucleic acid polymerase. Preferable substrates include but are not limited to nucleic acids and derivatives thereof, ribonucleotides, deoxyribonucleotides, peptides, amino acids, carbohydrates, lipids, ions, organic molecules, inorganic molecules, fluorogenic substrates, chromogenic substrates. For example, the composition of assay reagents may be suitable for performing a qualitative or quantitative assay for an analyte that is a) a reactant in or
b) an inhibitor of, or
c) an activator of, or
d) protein, or
e) an enzyme capable of catalyzing a chemical reaction that takes place as a result of combining a sample containing said analyte with the composition of assay reagents. To stabilize the composition of such assay reagents in a dry form, a substrate for an enzyme can be separated from at least one of the other assay reagents, at least one of the other assay reagents being, in a preferable embodiment, an enzyme capable of acting upon said substrate.

In all embodiments of the invention at least one first reagent and one second reagent form a pair wherein the first reagent is an enzyme and the second reagent is substrate of said enzyme and the pair is formed of a nucleic acid polymerase and substrate thereof. Typical substrates are nucleic acids or derivatives thereof, i.e. any molecule containing nucleic acid such as deoxyribonucleic acid or ribonucleic acid as well as any synthetic or naturally occurring substance that is structurally related to nucleic acids. Examples of synthetic nucleic acid derivatives include but are not limited to locked nucleic acid (LNA), peptide nucleic acid (PNA), phosphorothioate nucleic acids, nucleic acid covalently or uncovalently conjugated to at least one organic or inorganic molecule as well as chimeric molecules comprising naturally occurring nucleic acid monomers and monomers of nucleic acid derivatives.

According to all embodiments of the present invention, the assay reagents include a nucleic acid polymerase, suitably a thermostable DNA polymerase or a thermostable RNA polymerase. For example, it is possible that the composition of assay reagents is such that it can be used to perform a nucleic acid amplification reaction, for example the polymerase chain reaction (PCR). In such a case, one can stabilize the assay reagent composition by dispensing the DNA polymerase on a separate spot from at least some of the other reagents needed to perform the nucleic acid amplification reaction (see the experimental section).

According to preferred embodiments of the present invention, the assay reagents include nucleic acids or derivatives thereof, suitably oligonucleotides. For example, it is possible that the composition of assay reagents includes labelled and/or unlabelled oligonucleotides that are stabilized from degradation by an enzyme also present in the composition of assay reagents by physical separation from the enzyme. If the reagent composition is suitable for performing PCR, for example, then the assay reagents can be stabilized by physically separating the nucleic acid assay reagents from the rest of the assay reagents as described in the present invention. The method can also be applied to stabilize the reagents needed to perform other nucleic acid amplification reactions, including but not limited to reverse transcriptase PCR, nucleic acid sequence based amplification (NASBA), strand displacement amplification (SDA), ligase chain reaction (LCR) or the rolling circle amplification (RCA).

In one preferred embodiment of the invention the first reagent is a reverse transcriptase. For example, the assay reagent composition may be suitable for performing a cDNA synthesis reaction or a reverse transcription PCR (RT-PCR) reaction. In such a case, the assay reagent composition may be stabilized in a dry form by physically separating the reverse transcriptase from at least one of the other assay reagents.

Figure 4:
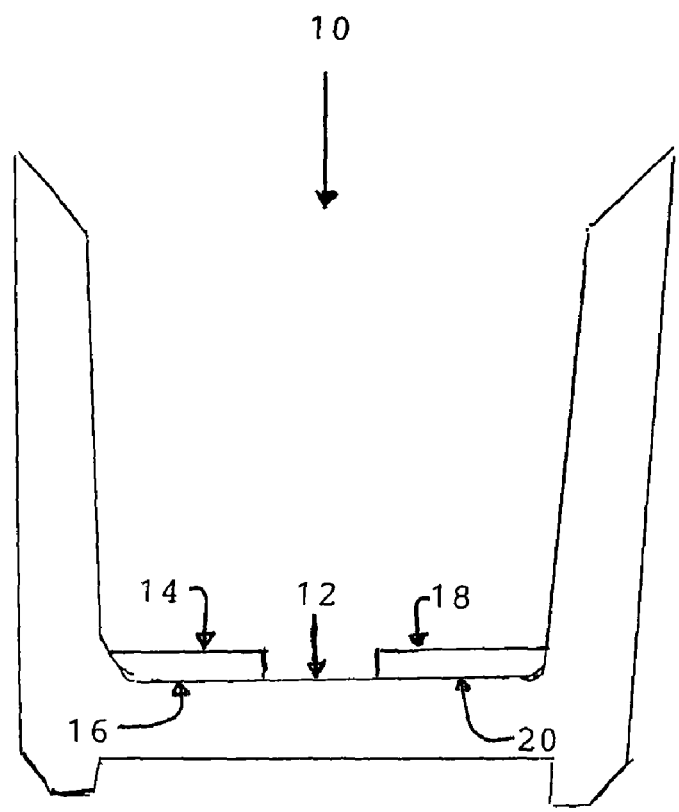
FIG. 4 shows a cross-section of a reagent container of the present invention.

Referring to FIG. 4, reagent container 10 includes an inner surface 12, with a first reagent 14 having been dried onto first area 16 of inner surface 12, and a second reagent 18 having been dried onto second area 20 of inner surface 12, with second area 20 distinctly separate from first area 16.

The reagent container can comprise more than one pair of reagents, each pair consisting of a first and a second reagent used in the detection of a biological and/or chemical analyte, and the first reagent of each pair has been dried onto a first area for said pair, of the inner surface distinctly separate, i.e. without any overlap, from a second area for said pair, of the inner surface onto which the second reagent of the pair has been dried.

It is to be noted that the first area and/or the second area of any pair of reagents need not be the first area and/or second area of any other pair of reagents although they can be. Any first or second area of a pair can be a first or second area of another pair. It is, however, essential for the invention that interfering reagents are not in the same area, i.e. reagents the stability of which is essentially compromised during drying and/or storing if present in the same area.

The reagent container can be for the detection of more than one biological and/or chemical analyte and the reagent container can comprise one or more pairs of reagents, each pair consisting of a first and a second reagent, for a biological and/or chemical analyte, same or different for each pair, to be detected and/or quantified, and the first reagent of each pair can be dried onto a first area for said pair, of the inner surface distinctly separate, i.e. without any overlap, from a second area for each pair, of the inner surface onto which the second reagent of the same pair can been dried.

According to some embodiments of the invention a further first reagent is a binding agent and a further second reagent is a ligand of said binding agent.

In other embodiments of the invention with several pairs of reagents a further first reagent can be an antibody. For example, the assay reagent composition may be suitable for performing an immunoassay reaction, suitably a competitive immunoassay or a non-competitive immunoassay. In such a case, the assay reagent composition may be stabilized in a dry form by physically separating at least one of the assay components from the rest of the assay components. For example, one can separate a labelled antibody or a labelled ligand of an antibody from at least one of the other assay reagents needed to perform the assay. For example, separating an antibody from a labelled ligand prevents the formation of antibody-ligand complexes prior to addition of a sample, which would compromise the performance of a competitive immunoassay. Also, separating a labelled or unlabelled antibody from the rest of the reagents in a competitive or non-competitive immunoassay may reduce the background signal measured in the assay, thus improving assay sensitivity.

In preferred embodiments all reagents of the analysis of each analyte, excluding the sample and optionally buffer, have been dried onto the inner surface of the reagent container.

The areas distinctly separate to which the reagents have been dried onto typically are dots with a diameter from 1 μm to 2 cm, preferably from 0.1 mm to 5 mm.

Many of the typical embodiments of the method of the present invention correspond to those of the reagent container as disclosed above.

In one preferred embodiment of the method of the present invention excess water is removed by air-drying or lyophilisation in step b) of the method.

EXPERIMENTAL SECTION

Example 1

Stabilization of Dried Real-Time PCR Reagents

Materials and Methods

A closed-tube PCR assay was set up for *Bacillus subtilis*. Table 1 shows the sequences and modifications of all primer (SEQ ID NO: 1 ja 2) and probe (SEQ ID NO: 3 ja 4) oligonucleotides. The PCR assay chemistry, which is based on the use of lanthanide labelled probes, has been described by Nurmi et al. (2002). All PCR amplifications were performed in a volume of 30 μl containing 1× HotMaster Taq Buffer (Eppendorf, Germany); 2.5 mM $MgCl_2$; 0.2 mM dNTPs; 0.3 μM forward and reverse primers; 28 nM lanthanide labelled probe; 280 nM quencher probe and 1.25 units of HotMaster Taq polymerase (Eppendorf, Germany).

TABLE 1

| | Oligonucleotides | | |
|---|---|---|---|
| Oligonu-cleotide | SEQ ID NO | Sequence from 5' to 3' | Label/end position |
| B. subtilis 5'primer | 1 | GCGGAGCAAGCTTCGTACCTTCT | None |
| B. subtilis 3'primer | 2 | CTAACGCCCAGAACACCGATTGAGT | None |
| B. subtilis probe | 3 | CCATACCAGGACGGCAGTTCTCAGC | Eu/5' |
| B. subtilis quencher | 4 | CTGCCGTCCTGGTATGG | QSY-7/3' |
| mmPSA 5' primer | 5 | TGAACCAGAGGAGTTCTTGCA | None |
| mmPSA 3' primer | 6 | CCCAGAATCACCCGAGCGA | None |
| mmPSA probe | 7 | MCCTTCTGAGGGTGATTGCGCACTG | Tb/5' |

TABLE 1-continued

| | Oligonucleotides | | |
|---|---|---|---|
| Oligonu-cleotide | SEQ ID NO | Sequence from 5' to 3' | Label/end position |
| mmPSA quencher | 8 | AATCACCCTCAGAAGGMT | QSY-7/3' |

[1]M, amino modified cytosine
[2]Bold letters denote bases that are not complementary to the target sequence.

To make dry PCR wells, PCR mixtures containing all other PCR reagents except template DNA were prepared and dispensed on plastic reaction wells. To investigate the stabilizing effect of separating the DNA polymerase from the other assay components, reaction mixtures were also prepared that contained all other assay components except the DNA polymerase and the DNA template. The mixtures containing no DNA polymerase were dispensed on a plastic reaction well and, onto a different location in the same well, the DNA polymerase was dispensed in a volume of 0.3 μl in such a manner that the polymerase containing liquid was not in contact with the rest of the reagents. Excess water was removed from all wells by air-drying at room temperature.

To demonstrate the stability of dried PCR reagents, their performance was tested by adding a DNA template in a volume of 30 μl of sterile water. Upon sample addition, the dried assay reagents were thus dissolved. After sealing the reagent wells, they were subjected to a thermal cycling protocol consisting of 43 cycles of 15 seconds at 95° C.; 1 minute at 60° C.; and 15 seconds at 55° C. The amplifications were monitored by measuring time-resolved europium fluorescence at the low (55° C.) temperature at selected PCR cycles, as described by Nurmi et al. (2002). Signal-to-noise ratios were calculated for all europium fluorescence measurements by dividing each europium signal by the average europium signal obtained from the same PCR well in the three first measurements.

Results and Discussion

FIG. 1 shows the instability of PCR reagents dried as a mixture. The figure shows the europium signal-to-noise ratios (on the y-axis) obtained at PCR cycles 21-43 (on the x-axis) measured from PCR reactions that were prepared using pre-dried PCR reagents that had been dried as mixtures containing all PCR components, including the DNA polymerase. PTC 1 (filled triangles) and PTC 2 (filled diamonds) denote positive control reactions, into which *Bacillus subtilis* DNA was added as template. NTC 1 (open triangles) and NTC 2 (open diamonds) denote negative control reactions, into which pure water instead of template DNA was added. The positive control reactions give amplification plots that are no different from the plots obtained for negative control reactions: there is no amplification signal, indicating that the PCR reagents dried as a mixture containing all PCR components, including the DNA polymerase, were not stable.

Figure 2:
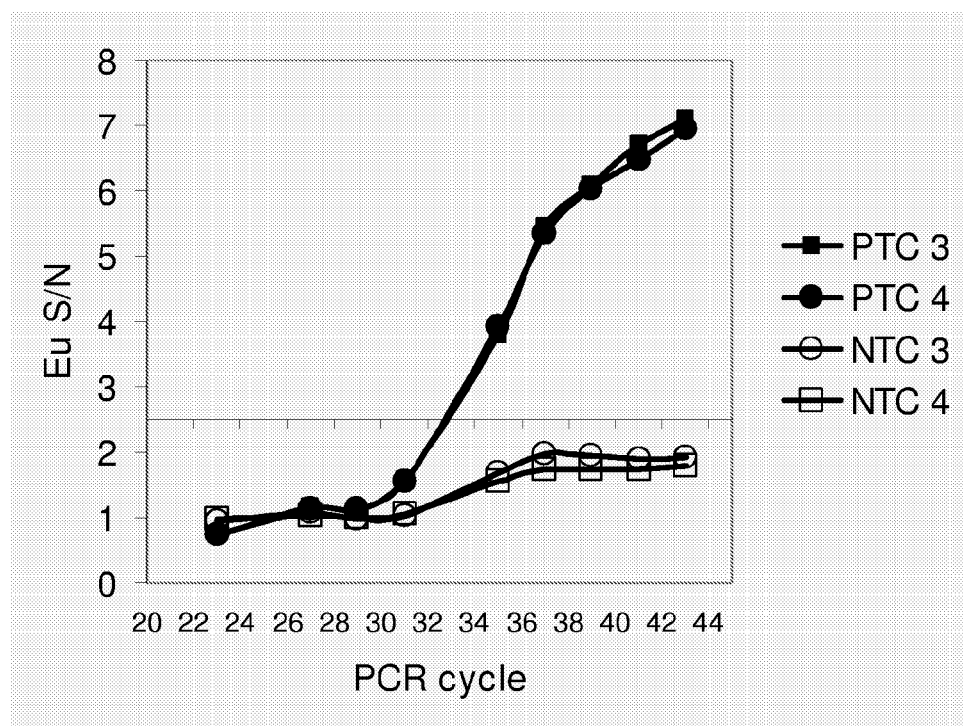
FIG. 2 shows stability of PCR reagents dried by separating the DNA polymerase from the rest of the assay reagents.

FIG. 2 shows the stability of PCR reagents dried by separating the DNA polymerase from the rest of the assay reagents. The figure shows the europium signal-to-noise ratios (on the y-axis) obtained at PCR cycles 23-43 (on the x-axis) measured from PCR reactions that were prepared using pre-dried PCR reagents that had been dried in two separate dots, a first dot containing the DNA polymerase and a second dot containing the nucleotides, buffer, primer and probe oligonucleotides. PTC 3 (filled squares) and PTC 4 (filled circles) denote positive control reactions, into which *Bacillus subtilis* DNA was added as template. NTC 3 (open circles) and NTC 4 (open squares) denote negative control reactions, into which pure water instead of template DNA was added. The positive control reactions give amplification plots that are clearly different from the plots obtained for negative control reactions: there is a clear amplification signal, indicating that the PCR reagents, when dried as two separate dots, were stable.

FIGS. 1 and 2 show the effect of separating the DNA polymerase from the rest of the PCR reagents. When the assay reagents were dried as a mixture, the mixtures were not stable and no target DNA amplification could be detected (FIG. 1). A clear amplification signal was only obtained from reaction wells in which the DNA polymerase was separated from the rest of the reagents (FIG. 2). This is probably explained by an adverse reaction catalysed by the DNA polymerase during drying. Already at the beginning of amplification, the absolute europium fluorescence signals obtained from the reactions that were prepared without separation of the DNA polymerase were significantly higher than in the reactions where the DNA polymerase had been dried separated from the rest of the reagents. It is therefore likely that, during drying, the DNA polymerase exerted an adverse function, possibly a nucleolytic attack, on one or all of the oligonucleotides present in the reagent mixture. This kind of behaviour could be explained by the fact that during drying, the concentrations of all reagents increase up to a very high level before all excess water has been removed. At such high concentrations of enzyme, nucleotides, electrolytes and oligonucleotides, unpredictable reactions may occur.

Example 2

Stabilization of Dried cDNA Synthesis Reagents

Materials and Methods

Reverse transcription reactions were performed using the High-Capacity cDNA Archive Kit (Applied Biosystems, USA) to reverse transcribe a constant amount (à 10 000 molecules) of mmPSA, which is an in vitro synthesized RNA species (Nurmi et al., 2002). As negative controls, reactions were also performed that contained water instead of template RNA. Three types of reactions (a-c) were prepared and compared:
  a. Normal cDNA synthesis reactions (10 µl volume) that were prepared and performed according to the instructions provided by the manufacturer.
  b. Dry chemistry reactions, where all reaction components except for the template RNA (buffer, dNTPs, random sequence oligonucleotides primers and reverse transcriptase) were pre-dispensed to the bottom of a reaction vessel and excess water was removed by air-drying. Sample RNA was added in a volume of 10 µl of water.
  c. Dry chemistry reactions that were prepared and performed as above (b) except that the reverse transcriptase was dispensed and dried onto a distinct spot on the bottom of the reaction vessel, there being no overlap between the areas occupied by the reverse transcriptase and the rest of the cDNA synthesis reagents (ie. buffer, nucleotides and random sequence oligonucleotides primers).

To analyze the cDNA synthesis efficiencies in the different cases, 2.5 µl cDNA samples obtained in the three different manners described above were analysed in real-time PCR reactions. The 10 µl amplification reactions consisted of 1× HotMaster buffer (Eppendorf, Germany), 0.15 mM dNTPs, 0.075 µM forward and reverse primers, 0.12 µM terbium probe, 1.2 µM quencher probe and 0.25 U HotMaster DNA polymerase (Eppendorf). The sequences and modifications of all primer and probe oligonucleotides are shown in table 1 (Nurmi et al. 2002). All PCR reactions were performed in a single experiment on MicroAmp Optical Plates sealed with MicroAmp optical Caps (Applied Biosystems). Thermal cycling (PTC 200 DNA Engine, MJ Research, USA) consisted of the following segments: 10 cycles of denaturation at 95° C. for 15 seconds followed by primer annealing and extension and probe digestion at 63.5° C. for 1 minute; 8 cycles of denaturation at 95° C. for 15 seconds followed by primer annealing and extension and probe digestion at 61.5° C. for 1 minute; 23 cycles of denaturation at 95° C. for 15 seconds followed by primer annealing and extension and probe digestion at 61.5° C. for 1 minute. In cycles 19, 21, 23, 25, 27, 29, 31, 33, 35, 37, 39 and 41 (i.e. cycles 1, 3, 5, 7, 9, 11, 13, 15, 17, 19, 21 and 23 of the last segment) the temperature was lowered to 35° C. for 15 seconds after the annealing/extension/probe digestion step. At this lower temperature, the time-resolved terbium fluorescence intensities of all reactions were recorded using a Victor 1420 Multilabel Counter (Perkin-Elmer Life and Analytical Sciences, USA). Signal-to-noise ratios were calculated for all terbium fluorescence measurements by dividing each terbium signal by the average terbium signal obtained from the same PCR well in the two first measurements (at PCR cycles 19 and 21).

Results and Discussion

Figure 3:
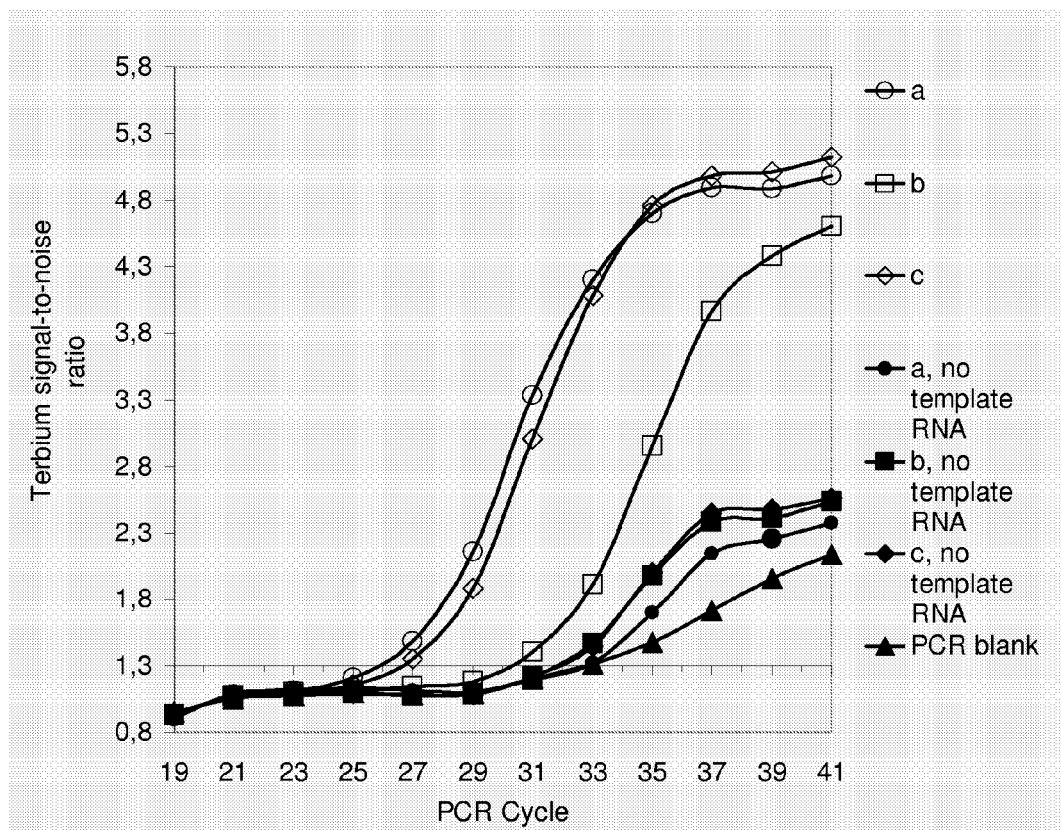
FIG. 3 shows stability of dried cDNA synthesis reagents dried altogether or by separating the reverse transcriptase compared to liquid reagents.

FIG. 3 and table 2 show how cDNA synthesis reagents can be stabilized in dry form by drying the reverse transcriptase onto a spot that is separate from the rest of the reagents.

FIG. 3 shows stabilization of dried cDNA synthesis reagents. The amplification plots were generated using as PCR template cDNA that was synthesis starting from à 10 000 molecules of mmPSA RNA (open symbols) or, in negative control reactions, no RNA template at all (closed symbols). Three different kinds of cDNA synthesis reactions were performed: in a), a normal cDNA synthesis was performed according to the instructions provided by the manufacturer (circles); in b) all cDNA synthesis reagents were dried as a mixture (squares) and in c) the reverse transcriptase enzyme and the rest of the cDNA synthesis reagents were dried on separate spots (diamonds). Each cDNA synthesis reaction was performed in three replicate tubes and each cDNA sample was analyzed in two replicate PCR amplification reactions; each curve in the figure represents the average terbium signal-to-noise ratios obtained from the resulting six replicate PCR amplifications. The PCR blank (triangles) was a negative PCR control containing only water as template and represents the average of two replicate reactions. As can be seen in the figure, separation of the reverse transcriptase from the rest of the reagents (c) gives comparable results with the normal cDNA synthesis procedure using liquid reagents (a), whereas if the reagents are dried as a mixture (b), cDNA synthesis efficiency is very low.

Amplification plots from PCR reactions containing as templates the cDNAs obtained using the three different methods (a-c) described under materials and methods are shown in FIG. 3. As can be seen, the performance of dried reagents, when stabilized by dispensing the reverse transcriptase onto a separate spot, is equal or almost equal to the normal reagents that were not dried. Instead, if the reaction mixture is dried without separating the reverse transcriptase from the rest of the reagents, assay performance drops dramatically. In the FIG. 3, this is visible as the amplification curve, which shows terbium fluorescence signal-to-noise ratio on the y-axis and the number of PCR cycles on the x-axis, crossing the threshold value of 1.3 at a much later PCR cycle than when the reagents are stabilized or when fresh reagents are used.

Table 2 shows the threshold cycles values obtained using cDNA reagent mixtures prepared in three different ways. Each cDNA synthesis reaction was performed in three replicate tubes and each cDNA sample was analyzed in two replicate PCR amplification reactions; the average threshold cycle value obtained from six replicate reverse transcription-PCR amplifications is shown for each case. The threshold cycle ($C_t$) values, or the PCR cycle numbers at which fluorescence signal-to-noise ratios cross the threshold value, are shown for the different reactions. The $C_t$ value is inversely related to the ten-base logarithm of the initial template copy number in PCR: therefore, the higher the threshold cycle is, the less cDNA was present in the PCR vessel at the beginning of amplification. Therefore, the more efficient the cDNA synthesis was, the lower is the $C_t$ value. It can be seen in table 2 that the efficiency of reverse transcription was highest when fresh reagents were used and almost as high when the reagents were stabilized by drying the reverse transcriptase onto a separate spot from the rest of the reagents; however, the cDNA synthesis efficiency is clearly inferior when all reagents were dried as a mixture. This may be explained, for example, by partial inactivation of the reverse transcriptase when dried together with the other cDNA synthesis reagents or by adverse reactions catalyzed by the reverse transcriptase during drying. It is therefore clear that the method according to the present invention allows preservation of cDNA synthesis reagents in a dry form.

TABLE 2

Threshold cycles values obtained.

| cDNA synthesis reaction type | $C_t$ |
|---|---|
| Normal (a) | 25.9 |
| Dried reagents (b) | 30.3 |
| Dried reagents, enzyme separated (c) | 26.7 |
| Normal (a), no template RNA | 32.8 |
| Dried reagents (b), no template RNA | 31.8 |
| Dried reagents, enzyme separated (c), no template RNA | 31.9 |
| PCR blank | 32.7 |

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Compton J. (1991) Nucleic acid sequence-based amplification. *Nature.* 350(6313):91-2.
Fredriksson S, Gullberg M, Jarvius J, Olsson C, Pietras K, Gustafsdottir S M, Ostman A, Landegren U. (2002) Protein detection using proximity-dependent DNA ligation assays. Nat Biotechnol. 20(5):473-7.
Higuchi R, Dollinger G, Walsh P S, Griffith R. (1992) Simultaneous amplification and detection of specific DNA sequences. *Biotechnology (N Y).* 10(4):413-7.
Higuchi R, Fockler C, Dollinger G, Watson R. (1993) Kinetic PCR analysis: real-time monitoring of DNA amplification reactions. *Biotechnology (N Y).* 11(9):1026-30.
Lövgren T, Pettersson K. One-step all-in-one dry reagent immunoassay. WO9738311
Lövgren T, Meriö L, Mitrunen K, Mäkinen M L, Mäkelä M, Blomberg K, Palenius T, Pettersson K. (1996) One-step all-in-one dry reagent immunoassays with fluorescent europium chelate label and time-resolved fluorometry. *Clin Chem.* August; 42(8 Pt 1):1137-9.
Niemeyer C M, Adler M, Wacker R. (2005) Immuno-PCR: high sensitivity detection of proteins by nucleic acid amplification. Trends Biotechnol. 23(4):208-16.
Nurmi J, Kiviniemi M, Kujanpää M, Sjöroos M, llonen J, Lövgren T. (2001) High-throughput genetic analysis using time-resolved fluorometry and closed-tube detection. *Anal. Biochem.* 299:211-217.
Nurmi J, Wikman T, Karp M, Lövgren T. (2002) High-performance real-time quantitative RT-PCR using lanthanide probes and a dual temperature hybridization assay. *Anal Chem.* 74(14):3525-32.
Saiki R K, Scharf S, Faloona F, Mulli K B, Horn G T, Erlich H A, Arnheim N (1985) Enzymatic amplification of beta-globin genomic sequences and restriction site analysis for diagnosis of sickle cell anemia. *Science* 230:1350-4.

The invention claimed is:

1. A reagent container for detection and/or quantitation of at least one biological or chemical analyte from a sample, said reagent container comprising an inner surface enclosing a volume, wherein volume analytical reactions of at least one analysis for detection and/or quantitation of at least one analyte take place, and at least two reagents of an analysis of an analyte have been dried onto said inner surface and at least a first said reagent has been dried onto a first area of the inner surface distinctly separate from a second area of the inner surface onto which at least a second said reagent has been dried, wherein the first reagent and the second reagent form a pair wherein the first reagent is an enzyme and the second reagent is a substrate of said enzyme, and said pair consists of a nucleic acid polymerase and substrate thereof.

2. The reagent container according to claim 1 wherein the first reagent is a reverse transcriptase.

3. The reagent container according to claim 1 wherein the reagent container comprises more than one pair of reagents, each pair consisting of a first and a second reagent, of a biological and/or chemical analyte to be detected, and the first reagent of each pair has been dried onto a first area for said pair, of the inner surface distinctly separate from a second area for said pair, of the inner surface onto which the second reagent of the pair has been dried.

4. The reagent container according to claim 1 wherein the reagent container is for the detection of more than one biological and/or chemical analyte and the reagent container comprises one or more pairs of reagents, each pair consisting of a first and a second reagent, for a biological and/or chemical analyte, same or different for each pair, to be detected, and the first reagent of each pair has been dried onto a first area for said pair, of the inner surface distinctly separate from a second area for each pair, of the inner surface onto which the second reagent of the same pair has been dried.

5. The reagent container according to claim 1 wherein all reagents of the analysis of each analyte, excluding the sample and optionally buffer, have been dried onto the inner surface of the reagent container.

6. The reagent container according to claim 1 wherein the areas distinctly separate to which the reagents have been dried onto are dots with a diameter from 1 μm to 2 cm.

7. A method for stabilising onto an inner surface of a reagent container dried assay reagents for the detection and/or quantitation of a biological or chemical analyte from a sample, said method comprising the steps of a) dispensing at least two reagents, a first reagent and a second reagent, needed in the detection of the analyte onto the inner surface of the reagent container, and b) removing excess water from the reagents, wherein in step a) the first reagent is dispensed onto a first area of the inner surface distinctly separate from a second area of the inner surface onto which the second reagent is dispensed wherein the first reagent and the second reagent form a pair wherein the first reagent is an enzyme and the second reagent is a substrate of said enzyme, and said pair consist of a nucleic acid polymerase and substrate thereof.

8. The method according to claim 7 wherein the first reagent is a reverse transcriptase.

9. The method according to claim 7 wherein the reagent container comprises more than one pair of reagents, each pair consisting of at least a first and a second reagent, of a biological and/or chemical analyte to be detected, and in step a) the first reagent of each pair is dispensed onto a first area for each pair of the inner surface distinctly separate from a second area for each pair of the inner surface onto which the second reagent of the same pair is dispensed.

10. The method according to claim 7 wherein the reagent container is for the detection and/or quantitation of more than one biological and/or chemical analyte, said reagent container comprising pairs of reagents consisting of at least a first and a second reagent for a biological and/or chemical analyte, same or different for each pair, to be detected and in step a) the first reagent of each pair is dispensed onto a first area for each pair of the inner surface distinctly separate from a second area for each pair of the inner surface onto which the second reagent of the same pair is dispensed.

11. The method according to claim 7 wherein in step a) all reagents of the analysis of the analyte, or analyses of each analyte, excluding the sample and optionally a buffer, are dispensed onto the inner surface of the reagent container.

12. The method according to claim 7 wherein in step b) excess water is removed by air drying or lyophilization.

13. The reagent container according to claim 6, wherein said diameter is from 0.1 mm to 5 mm.

* * * * *